(12) United States Patent
Jurna et al.

(10) Patent No.: US 10,518,103 B2
(45) Date of Patent: Dec. 31, 2019

(54) SKIN TREATMENT DEVICE FOR LOCALLY TREATING SKIN

(71) Applicant: KONINKLIJKE PHILIPS N.V., Eindhoven (NL)

(72) Inventors: Martin Jurna, Eindhoven (NL); Jonathan Alambra Palero, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 90 days.

(21) Appl. No.: 15/129,847

(22) PCT Filed: Apr. 1, 2015

(86) PCT No.: PCT/EP2015/057187
§ 371 (c)(1),
(2) Date: Sep. 28, 2016

(87) PCT Pub. No.: WO2015/150460
PCT Pub. Date: Oct. 8, 2015

(65) Prior Publication Data
US 2017/0136257 A1    May 18, 2017

(30) Foreign Application Priority Data

Apr. 1, 2014    (EP) .................................... 14163091

(51) Int. Cl.
*A61N 5/06*    (2006.01)
*A61N 5/067*    (2006.01)

(52) U.S. Cl.
CPC ...... *A61N 5/0616* (2013.01); *A61N 2005/067* (2013.01); *A61N 2005/0644* (2013.01)

(58) Field of Classification Search
CPC .......... A61N 5/0616; A61N 2005/0644; A61N 2005/067; A61B 18/20; A61B 18/203;
(Continued)

(56) References Cited

U.S. PATENT DOCUMENTS 6,050,990 A * 4/2000 Tankovich ........... A61B 18/203
606/16
7,160,287 B1 * 1/2007 Siegel .................. A61B 18/203
606/3
(Continued)

FOREIGN PATENT DOCUMENTS

JP        8243181 A      9/1996
WO    WO 03/049633    *   6/2003  ........... A61N 5/0616
(Continued)

*Primary Examiner* — Carl H Layno
*Assistant Examiner* — Erin M Piateski (57) ABSTRACT

A skin treatment device for locally treating skin with light is provided that comprises a tip, a light emission element, a safety mechanism comprising an optical element and an optical element positioning structure. The optical element receives a converging light beam from the light emission element. The optical element is configured to operate as a diverging lens. The optical element positioning structure positions the optical element in a safety position, or in a treatment position when the tip is in contact with the skin to be treated, and allows movement of the optical element between both positions. In the safety position, the optical element is arranged at a position on the optical axis to generate an eye-safe light beam. In the treatment position, the optical element is arranged at another position on the optical axis to generate a treatment light beam.

20 Claims, 6 Drawing Sheets

(58) Field of Classification Search
CPC .............. A61B 2017/00747–00774; A61B
2017/00982; A61B 2017/00991; A61B
2018/00452–00476; A61B
2018/00916–00946; A61B 2018/1807;
A61B 2018/2015; A61B 2018/202; A61B
2018/2023; A61B 2018/2035; A61B
2018/20553; A61B 2018/2255–2266;
A61B 2090/049
USPC ....................................................... 606/9–14
See application file for complete search history.

(56) References Cited

U.S. PATENT DOCUMENTS

| | | | |
|---|---|---|---|
| 7,184,614 B2* | 2/2007 | Slatkine | A61B 18/20 |
| | | | 606/9 |
| 9,283,037 B2* | 3/2016 | Bragagna | A61B 18/203 |
| | | | 606/9 |
| 2004/0176754 A1 | 9/2004 | Island | |
| 2007/0083190 A1* | 4/2007 | Domankevitz | A61B 18/203 |
| | | | 606/9 |
| 2008/0027518 A1 | 1/2008 | Island | |
| 2008/0140164 A1 | 6/2008 | Oberreiter | |
| 2011/0040358 A1 | 2/2011 | Bean | |
| 2012/0323229 A1 | 12/2012 | Zenzie | |
| 2013/0317571 A1 | 11/2013 | Gerlitz | |

FOREIGN PATENT DOCUMENTS

| | | |
|---|---|---|
| WO | 2008008971 A1 | 1/2008 |
| WO | 2010045973 A1 | 4/2010 |
| WO | 2012106678 A1 | 8/2012 |

* cited by examiner

SKIN TREATMENT DEVICE FOR LOCALLY TREATING SKIN

This application is the U.S. National Phase application under 35 U.S.C. § 371 of International Application No. PCT/EP2015/057187, filed on Apr. 1, 2015, which claims the benefit of International Application No. 14163091.3 filed on Apr. 1, 2014. These applications are hereby incorporated by reference herein.

FIELD OF THE INVENTION

The invention relates to the field of skin treatment devices and safety solutions for such devices. More in particular, the application relates to the field of precision light-based skin treatment devices in which a relatively narrow beam of light is used to locally treat the skin.

BACKGROUND OF THE INVENTION

Different types of light-based skin treatment devices are known that can treat different targets within the skin. These light-based devices use low or medium power light sources, like LED's, or relatively high power light sources, like IPL (intense pulsed light) and laser. With the low and medium power light sources certain targets within the skin, like fibroblast cells, can be stimulated to enhance the production of collagen tissue. Relatively high power light sources heat specific targets in the skin, like melanin, blood or water to induce local damages. These light-based skin treatments are dependent on the wavelength absorption profile of the selected target objects in the skin and are known as "selective photothermolysis". Fractional laser treatment devices have the purpose of non-ablative fractional photothermolysis of the targeted skin tissue, in particular by heating the water in the targeted skin tissue, for example, to thermally denature the collagen tissue in the dermis. In these fractional laser treatments, laser pulses create microscopic treatment zones (MTZs) of thermally denatured skin tissue surrounded by thermally undamaged tissue. This boosts skin repair mechanisms and improves skin appearance. Denatured collagen will be replaced in time, typically between one and three months, by new collagen. This will result in a reduction of wrinkles and fine lines. As an additional benefit the cells in the epidermis are damaged and replaced within several days. This replacement of the epidermal cells will result in a more even skin tone and an overall increase of the radiance or glow of the skin. Furthermore, fractional skin treatment devices are known that are ablative in that they completely remove the tissue in the micro-zones. Currently these ablative devices are less suitable for home-use, but are used in professional environments. Light is not only used to treat skin tissue, but is also used to achieve temporary hair growth reduction. In this application a broadband IPL (intense pulsed light) flash is used to damage the hair follicle and stop or reduce the hair growth. In this application, selective photothermolysis is obtained by matching the IPL wavelength spectrum and the duration of the light flashes to the absorption spectrum and thermal relaxation time of melanin, which is present in a large amount in hair tissue. Furthermore, IPL can be used to reduce the visibility of pigmented spots.

Both above mentioned solutions are based on large aperture devices to efficiently treat relatively large areas of interest. However, there is a growing interest in devices that offer improved precision, for example pen-like devices, by means of which spot treatments are achieved. A pen-like device has often a relatively small tip. It is relatively difficult to design a device with such a small treatment tip that includes safety mechanisms providing a level of safety such that the device is suitable for home-use. The safety mechanism needs to prevent the skin treatment device from emitting a potentially unsafe intense light beam that may harm the human eye. It is common to all electronic devices to include an ON button which should be pressed by the user to enable a certain device component, e.g. turning on a light source. It is desired to have an additional safety mechanism.

Published patent application US2012/0323229 and, for example, also published patent application US2004/0176754 disclose safety means to detect whether a front side, having a light exit window, of a skin treatment device is close to or in contact with the skin. These safety means are, for example, based on a pressure sensor, mechanical switches or a reflectometer contact system or the like. Such safety means are relatively complex, and thus relatively expensive. When such safety means are to be miniaturized, these safety means become even more expensive and sensitive to damages.

SUMMARY OF THE INVENTION

It is an object of the invention to provide a better safety mechanism for a skin treatment device.

A first aspect of the invention provides a skin treatment device. Advantageous embodiments are defined in the dependent claims.

A skin treatment device in accordance with the first aspect of the invention comprises a tip, a light emission element and a safety mechanism. The tip is arranged and configured to be brought into contact with the skin. The light emission element is arranged and configured to emit, in use, a light beam towards the tip along an optical axis. The light beam is a converging light beam. The optical axis extends in a longitudinal direction of the skin treatment device through the tip. The safety mechanism is provided proximate to the tip and is arranged to receive the light beam. The safety mechanism comprises an optical element and an optical element positioning structure. The optical element is arranged on the optical axis and is configured to operate as a diverging lens and is arranged to be brought into contact with the skin. The optical element comprises, on a first side, a light exit surface and, on a second side opposite the first side, a light entrance surface for receiving the light beam. The optical element positioning structure is configured and arranged to position the optical element in a safety position or alternatively in a treatment position and to allow the optical element to move from the safety position to the treatment position along the optical axis and vice versa. The optical element positioning structure is configured to position the optical element in the treatment position when the tip is in contact with the skin and to position the optical element in the safety position when the tip is not in contact with the skin. In the safety position the light entrance surface is arranged in the light beam at a first position on the optical axis to obtain an eye-safe light beam at the light exit surface. In the treatment position the light entrance surface is arranged in the light beam at a second position on the optical axis at a distance from the first position to obtain a treatment light beam at the light exit surface.

The treatment light beam has in general a relatively high energy density. The skin treatment device only emits the light beam of the light emission element in the form of the treatment light beam when the tip of the skin treatment device is in contact with the skin that must be treated. Only then the optical element positioning structure moves the optical element into the treatment position. When the tip is not in contact with the skin, the optical element is moved by the optical element positioning structure into the safety position. In the safety position, the optical element refracts the light beam received from the light emission element into an eye-safe light beam. In general, an eye-safe light beam has a relatively low energy density. Thus, at different light emission angles of the light beam, the amount of emitted energy is relatively low. The eye-safe light beam has a lower energy density than the treatment light beam. When, undesirably, the eye-safe light beam is emitted towards an eye of a human (which is only possible when the skin treatment device is not in contact with skin), the light beam is more harmless for the eye than when the treatment beam would be emitted towards the eye. Thus, an optical safety mechanism is provided which reduces the risk of harming the eyes of a user.

Another advantage is that it is relatively easy to miniaturize the safety mechanism because it is not difficult to manufacture a small optical element that is small enough to be used at a tip of a skin treatment device. By virtue thereof, the safety mechanism can be relatively easily integrated into the tip of the skin treatment device. It is further prevented that electronics or electronic connections are required. The skin treatment device is safe by design.

The optical element is configured to operate as a diverging lens, which means that, seen along the optical axis, the optical element as a whole operates as a negative lens. In general, the skilled person would consider using a converging lens when, for example, characteristics of impinging light beams must be changed. The skilled person is biased against the use of negative lenses, because, in general, negative lenses do not provide a lot of flexibility because they are not well suited to focus a light beam to a focal point. As such, it is unexpected that a diverging lens is able to provide an advantageous effect in the skin treatment device. When, for example, the optical element is positioned in or close to the focal point of the light beam, the diverging effect of the optical element is almost cancelled out such that one may still obtain, for example, a sufficiently effective treatment light beam, while, when the optical element is not so close to the focal point of the light beam, the light is strongly diverged for, for example, obtaining the eye-safe light beam.

Optionally, the light beam emitted by the light emission element converges to a focal point on the optical axis. The treatment position is a position wherein the light entrance surface of the optical element is proximate to the focal point to obtain, at the light exit surface of the optical element, a treatment beam that is approximately a parallel light beam. In the treatment position, the light entrance surface may slightly deviate from the focal point to compensate, by means of the diverging character of the optical element, for the converging character of the light beam that is received from the light emission element.

Optionally, the safety position is a position in which the light entrance surface of the optical element is distant from the focal point to obtain, at the light exit surface of the optical element, an eye-safe light beam that diverges.

Optionally, the optical element positioning structure comprises a resilient element for applying a first force to the optical element in a first direction parallel to the optical axis and away from the light emission element towards the safety position. Optionally, the optical element is arranged at the tip to receive a force substantially in a second direction towards the treatment position when the tip is pressed to the skin for moving the optical element towards the treatment position. The second direction is substantially opposite to the first direction. Thus, according to these optional embodiments, the optical element positioning structure only uses mechanical elements for moving the optical element along the optical axis between the treatment position and the safety position, and vice versa. This is relatively fail-safe. By using a resilient element for pressing the optical element towards the safety position, the optical element has the tendency to move to the safety position and, thus, the skin treatment device emits the eye-safe light beam when not being pressed to the skin. Optionally, the resilient element is a spring.

Optionally, the optical element positioning structure comprises a housing comprising a front wall being arranged proximate to a skin contact surface of the tip for defining the safety position by limiting movement of the optical element in the first direction. The front wall comprises an opening for allowing the optical element to partially protrude from the housing if the optical element is arranged at the safety position. The housing further comprises a movement limiting wall arranged at a distance from the skin contact surface of the tip for defining the treatment position by limiting movement of the optical element in the second direction when the optical element is pressed to the skin. Thus, the means which define how far the optical element can move along the optical axis are also constituted by mechanical elements and, consequently, the safety position and the treatment position are well-defined and the safety mechanism is relatively fail-safe.

Optionally, the light entrance surface has a selected shape that acts as a diverging lens. Optionally, the light entrance surface is a surface of a recess on the second side of the optical element. In this embodiment the light entrance surface is a concave surface. On the second side of the optical element, the recess has a circular cross-sectional shape, and the circular cross-sectional shape has a first radius. In the safety position of the optical element, a radius of the light beam, at a position where the light beam impinges on the light entrance surface, is at least 80% of the first radius. Optionally, in the safety position of the optical element, the radius of the light beam, at a position where the light beam impinges on the light entrance surface, is in a range from 80% to 100% of the first radius. The circular cross-sectional shape is arranged symmetrically around the optical axis. When the impinging light beam has a radius that is about equal to the first radius of the circular cross-sectional shape of the recess, which acts as a diverging lens in the safety position of the optical element, the light beam is strongly diverged by the recess. In this optional embodiment, about the whole light beam emitted by the light emission element impinges on the light entrance surface, which prevents unwanted scattering or refracting effects at an edge of the light entrance surface or at locations outside the light entrance surface. When the light entrance surface, acting as a diverging lens, is a recess in the light entrance surface of the optical element, it is relatively easy to manufacture such a diverging lens. Optionally, the recess in the light entrance surface has approximately the shape of a semi-sphere. When the recess in the light entrance surface has such a shape, the diverging effect of the light entrance surface will be relatively large.

Optionally, the light exit surface of the optical element has a protruding, smooth, round shape. In this embodiment the light exit surface is a convex surface. When the light exit surface of the optical element has said protruding, smooth, round shape, the tip of the skin treatment device contacting the skin may be constituted by the light exit surface. Said smooth, round shape is comfortable when the light exit surface is in contact with the skin, and the user may move or glide the tip of the skin treatment device over the skin without causing discomfort. Optionally, the protruding, smooth, round shape is approximately a semi-sphere. This shape is very comfortable when the light exit surface is moved over the skin.

Optionally, in an embodiment wherein the light entrance surface is a spherically shaped recess that has said first radius, and wherein the light exit surface is spherically shaped and has a second radius, the second radius is at least three times larger than the first radius. The light exit surface having a protruding spherical shape acts as a converging lens. The optical element as a whole has a diverging character and, thus, the second radius is larger than the first radius to prevent that the light exit surface cancels out the diverging effect of the light entrance surface. The larger the second radius, compared to the first radius, the larger the diverging effect of the optical element. Optionally, the second radius is at least five times larger than the first radius. Optionally, the second radius is at least eight times larger than the first radius.

Optionally, the optical element is made of a light transmitting material having a refractive index that matches the refractive index of human skin. In particular, the refractive index of the light transmitting material is within a range from 80% to 120% of the refractive index of human skin. When the light exit surface of the optical element is in contact with the skin, the light exit surface refracts the light only to a limited extent as a result of the matched refractive indices. Thus, when the optical element, in the treatment position, is in contact with the skin, it is prevented that the light exit surface of the optical element has a significant influence on the convergence or divergence of the treatment light beam. In other words, when the optical element, in the treatment position, is in contact with the skin, the light entrance surface determines the convergence or divergence of the treatment light beam.

Optionally, the skin treatment device is pen-shaped and is configured to be operated by a hand of a user. Thus, the skin treatment device is relatively small and has a low weight. The fact that the device is pen-shaped provides the user with a better view on and around the area of the skin that is being treated. As a result of the relatively small tip of the device, the skin treatment device can be positioned on the skin with relatively high precision. Other advantages of a pen-shaped skin treatment device include lower production costs, a lower price for consumers, increased treatment efficiency due to improved targeting of the treatment area, improved ergonomics and easier handling.

Optionally, the light emission element comprises a laser for emitting the light beam and a lens for converging the light beam towards a focal point on the optical axis.

Optionally, the eye-safe light beam is a diverging light beam. In the case of a diverging light beam, the cross-sectional shape of the light beam becomes larger with an increasing distance from the skin treatment device. Thus, the eye-safety increases when the user increases the distance between his eyes and the skin treatment device, because the light energy is distributed along a larger cross-sectional area. Furthermore, in comparison with a parallel light beam, a diverging light beam has less energy per light emission angle. Optionally, a beam angle of the eye-safe light beam is larger than a beam angle of the light beam received by the optical element. Optionally, the beam angle of the eye-safe light beam is larger than 20°. Optionally, the beam angle of the eye-safe light beam is larger than 28°. Such relatively large beam angles provide a relatively widely diverging eye-safe light beam and, thus, the risk of harming eyes of a person is relatively low when the skin treatment device emits the eye-safe light beam. A beam angle is defined as the angle between light rays on opposite sides of the optical axis of the light beam, wherein said light rays have an intensity value that is half the maximum intensity value of a (central) light ray of the light beam.

Optionally, the treatment light beam is a substantially parallel light beam. It is to be noted that it is practically impossible to generate, when using laser light, an exactly parallel light beam. Therefore, in an optional embodiment, 'substantially parallel' means that a beam angle of the treatment light beam is smaller than 4°. Optionally, the beam angle of the treatment light beam is smaller than 2°. Optionally, a diameter of the treatment light beam, measured at the light exit surface, is smaller than 1 mm. Such treatment light beams are sufficiently effective to locally treat the skin with high precision, and all the energy emitted by the light emission element is concentrated in a relative narrow light beam to ensure effective treatment.

These and other aspects of the invention are apparent from and will be elucidated with reference to the embodiments described hereinafter.

It will be appreciated by those skilled in the art that two or more of the above-mentioned options, implementations and/or aspects of the invention may be combined in any way deemed useful.

Modifications and variations of the device can be carried out by a person skilled in the art on the basis of the present description.

It should be noted that items denoted by the same reference numerals in different Figures have the same structural features and the same functions. Where the function and/or structure of such an item have been explained, there is no necessity for repeated explanation thereof in the detailed description.

The Figures are purely diagrammatic and not drawn to scale. Particularly for clarity, some dimensions are exaggerated strongly.

DETAILED DESCRIPTION OF EMBODIMENTS

Figure 1:
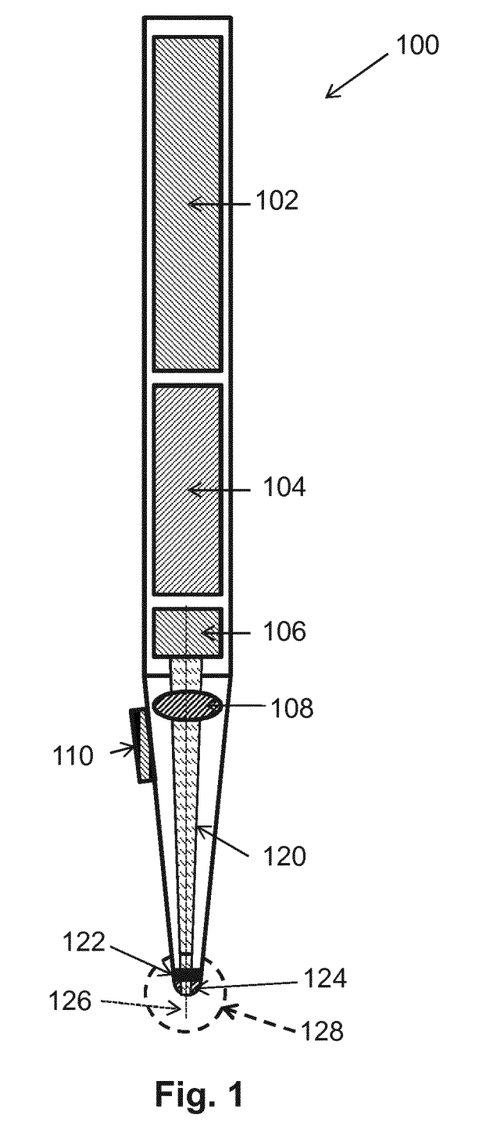
FIG. 1 schematically shows a cross-sectional view of a skin treatment device in accordance with the invention, FIG. 2a schematically shows a cross-sectional view of a tip of the skin treatment device of FIG. 1, wherein an eye-safe light beam is formed, FIG. 2b schematically shows a cross-sectional view of a tip of the skin treatment device of FIG. 1, wherein a treatment light beam is formed, FIG. 3a schematically shows a cross-sectional view of an embodiment of a safety mechanism wherein the optical element is arranged at a safety position, FIG. 3b schematically shows a cross-sectional view of the embodiment of the safety mechanism of FIG. 3a, wherein the optical element is arranged at a treatment position, FIGS. 4a to 4c schematically show a cross-sectional view of embodiments of an optical element of the safety mechanism of FIG. 3a, FIGS. 5a and 5b schematically shows results of a ray tracing simulation, wherein the optical element is positioned in the safety position and in the treatment position, respectively, FIG. 5c schematically shows results of a ray tracing simulation, wherein also a lens of the light emission element is taken into account, FIGS. 6a-6e schematically presents several results of ray-tracking simulations.

FIG. 1 schematically shows a cross-sectional view of a skin treatment device 100. The skin treatment device 100 is pen-shaped and its size and weight are such that it can be easily operated by a hand of a user. The user may use the skin treatment device 100 to treat the skin of another person or of an animal, or to treat his or her own skin. Although the presented skin treatment device 100 is pen shaped, other embodiments of the skin treatment device 100 may have another suitable shape for locally treating the skin.

The skin treatment device 100 comprises a battery 102, an electronic circuitry 104 for controlling operation of the skin treatment device 100 and/or driving a light source 106 (optionally a laser diode), which light source 106 is capable of generating a light beam, a focusing lens 108 which focuses the light beam generated by the light source 106 to a converging light beam 120 towards a focal point, a control switch 110, a tip 128 which comprises a safety mechanism comprising an optical element 124 and an optical element positioning structure 122. The light source 106, the focusing lens 108 and the optical element are arranged around an optical axis 126 that extends in the longitudinal direction of the skin treatment device 100. The light source 106 and the focusing lens 108 together form a light emission element of the skin treatment device 100 for generating the converging light beam 120. Embodiments of the skin treatment device are not limited to light emission elements as discussed above; other suitable light emission elements that generate converging light beam 120 may be used as well. Embodiments of the skin treatment device are not limited to pen-shaped skin treatment devices. However, the pen-shape provides specific advantages as discussed in this document.

A user may operate the control switch 110 to instruct the skin treatment device 100 to generate a light beam for treating the skin. The electronic circuitry 104 receives a signal from the control switch 110 and, subsequently, the electronic circuitry 104 may decide to drive the light source 106 such that a beam of light is generated. The light source 106 emits the beam of light towards the focusing lens 108 which transmits the converging light beam 120 towards the tip 128 of the skin treatment device 100. The converging light beam 120 has a focal point (not shown in FIG. 1) on the optical axis 126 close to the tip 128. The optical element 124 and the optical element positioning structure 122 together form a safety mechanism. The optical element positioning structure 122 positions the optical element 124 at such a location that, when the tip 128 is pressed to skin to be treated, a treatment light beam is generated which comprises a sufficient amount of energy in a relatively narrow light beam to locally treat the skin. The optical element positioning structure 122 positions the optical element 124 at such a location that, when the tip 128 is not pressed to the skin to be treated, an eye-safe light beam is generated which is relatively wide and in which the energy density per unit area (of a cross-section of the eye-safe light beam) is, in particular at a distance from the tip, relatively low, so that, when the user directs the eye-safe light beam towards eyes, the eyes are not harmed. Details and embodiments of the safety mechanisms are discussed in the subsequent Figures.

It is to be noted that eye safety does not only depend on the amount of light energy per light emission angle. In particular, when the light emission element uses a diode laser to generate the light, the wavelength and the pulse length are also important parameters that influence the eye safety of the eye-safe light beam. IEC-60825-1 and ANSI Z136.1 standards disclose methods of calculating maximum permissible exposure values. This document mainly focuses on a mechanism to influence the amount of light energy per light emission angle to obtain the treatment beam and to obtain the eye-safe light beam.

Figure 2A:
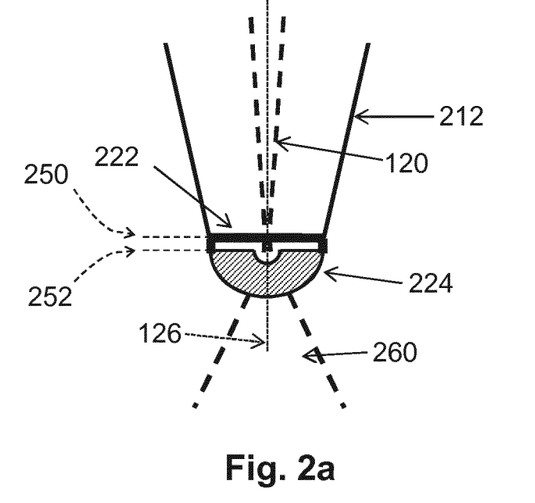

FIG. 2a schematically shows a cross-sectional view of a tip 128 of the skin treatment device 100 (of FIG. 1), wherein an eye-safe light beam 260 is formed. The tip comprises a portion of a housing 212 of the skin treatment device 100, and, in use, a converging light beam 120 passing through this portion is received by a safety mechanism. The safety mechanism comprises an optical element 224 and an optical element positioning structure 222. The optical element 224 is moveable along the optical axis 126 from a safety position 252 to a treatment position 250 and vice versa. The safety position 252 and the treatment position 250 are indicated in FIG. 2a as a line which coincides with a rear side of the optical element 224 when the optical element 224 is arranged in the specific positions. The rear side of the optical element 224 is a side that faces towards the interior of the skin treatment device and on which, in use, the converging light beam 120 impinges. The safety position 252 is distant from the focal point of the converging light beam 120, while the treatment position 250 is proximate to the focal point of the converging light beam 120. In particular, in the embodiment of FIG. 2a, seen in a direction away from the light emission element, the converging light beam 120 diverges after passing the focal point of the converging light beam 120. In an embodiment, the optical element 224 in the safety position 252 receives the light beam in an area where the light beam diverges.

In the example of FIG. 2a, the optical element has a relatively flat rear side in which a spherical recess is manufactured and has, at a front side, a spherically shaped surface that must be brought into contact with the skin to be treated. The surface of the spherical recess forms the light entrance surface. The spherically shaped surface at the front side is the light exit surface of the optical element. Because the spherical recess is relatively small with respect to the spherically shaped (front-) surface, the optical element as a whole acts as a diverging lens. At the safety position 252, the impinging light beam 120 diverges and the optical element 224 diverges the light beam further to obtain a diverging eye-safe light beam 260. Thus, the amount of energy present in the light generated by the light emission element is distributed along a large number of light emission angles and, as such, light rays of the eye-safe light beam 260 emitted in a particular light emission direction have a relatively low energy level such that, when they impinge on an eye, they do not harm the eye.

Figure 2B:
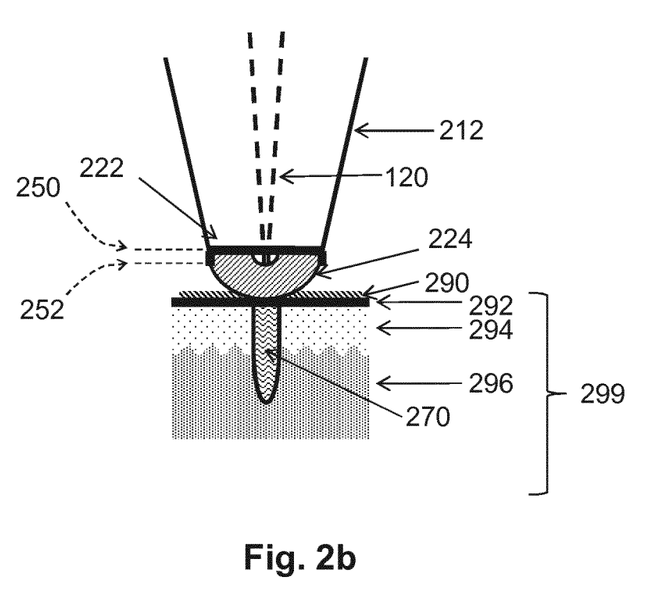

FIG. 2b schematically shows a cross-sectional view of a tip of the skin treatment device wherein a treatment light beam 270 is formed. In the example of FIG. 2b, the tip of the skin treatment device is pressed against skin 299 of a user. In the specific example of FIGS. 2a and 2b, the outermost part of the tip is formed by a surface of the optical element 224. The optical element positioning means 222 is configured to position the optical element 224 at the treatment position 250 when the surface of the optical element is pressed against the skin 299.

In the treatment position, the spherical recess in the rear side of the optical element is proximate to the focal point of the converging light beam 120. At this point the strongly divergent character of the spherical recess is cancelled out, or is used to a limited extend to compensate for the converging character of the converging light beam 120. As a result, a relatively narrow treatment light beam 270 is formed which has a relatively high energy density. The treatment light beam 270 comprises, for example, substantially parallel oriented light rays within a beam that has a radius that is smaller than, for example, 1 mm. It might also be that the treatment light beam 270 has a slightly diverging character, but then the beam angle of the treatment light beam should be small, for example, not larger than 4° or, in another example, not larger than 2°.

In FIG. 2b, several layers of the skin 299 are shown. A top layer is the stratum corneum 292, below which the epidermis 294 is present and below the epidermis 294 is the dermis 296. The relatively narrow and sufficiently powerful treatment light beam 270 is able to penetrate the stratum corneum 292 and epidermis 294 layers and is for the largest part absorbed in the dermis 296 to obtain a treatment effect. Optionally, a gel or liquid 290 may be provided on the skin 299 to obtain better optical contact between the optical element 224 and the skin 299. The gel or liquid may be an index-matching gel or fluid whose refractive index approximately matches the refractive index of the optical element 224 and the refractive index of the skin 299 such that at the interfaces between optical element 224 and the gel or liquid and/or at the interfaces between the liquid or gel and the skin 299 the light rays of the treatment beam 270 are not much refracted. In an embodiment, the optical element 224 is made of a material that has a refractive index that is matched to the refractive index of the skin 299. In the above, refractive indices of different materials are matched "approximately" to each other, which means that they do not deviate more than 20% from each other, or, in another embodiment, that they do not deviate more than 10% from each other.

Figure 3A:
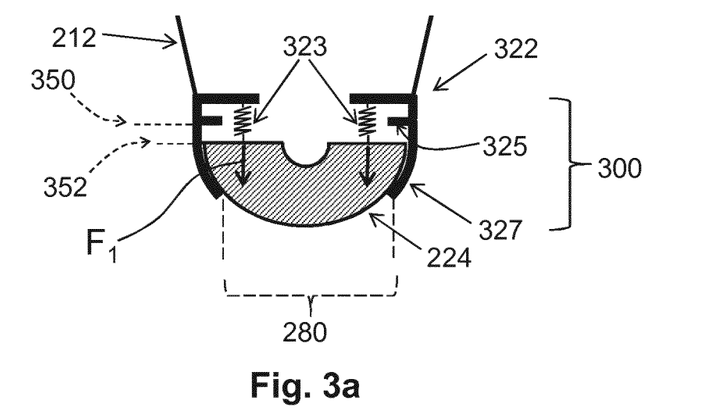

FIG. 3a schematically shows a cross-sectional view of an embodiment of the safety mechanism 300 wherein the optical element is arranged at a safety position 352. The safety mechanism 300 is arranged at a tip of a skin treatment device, for example, the tip 128 of skin treatment device 100 of FIG. 1. The safety mechanism 300 is coupled to a housing 212 of the skin treatment device 100. The safety mechanism 300 comprises an optical element 224 and an optical element positioning structure 322. Characteristics of the optical element 224 have already been discussed in the context of FIGS. 2a and 2b and other embodiments of the optical element 224 will be discussed in the context of FIGS. 4a to 4c. The optical element positioning structure 322 partly encloses the optical element 224 with a front wall 327 and comprises a position limiting wall 325. The front wall 327 and the position limiting wall limit movement of the optical element 224 along the optical axis. The front wall 327 has an opening 280 through which a portion of the optical element 224 may protrude for emitting a light beam. When the optical element 224 is in contact with the front wall 327 and maximally protrudes from the opening 280, the optical element 224 is in the safety position 352. The front wall 327 is designed such that, when the optical element 224 is in the safety position 352, the spherical recess on the rear side of the optical element 224 is distant from the focal point of the light beam that impinges on the spherical recess and, thus, the optical element 224 strongly diverges the impinging light beam, thereby forming the eye-safe light beam. The optical element positioning structure 322 also comprises, in the example of FIG. 3a, springs 323 which apply a first force $F_1$ to the optical element in a first direction towards the safety position 352, and hence towards the opening 280. Thus, the springs 323 force the optical element 224, when no other external forces are applied to the optical element 224, to move towards the safety position 352. It is to be noted that in the example of FIG. 3a, springs apply the first force $F_1$ to the optical element 224, but other resilient elements may also be used to apply the first force $F_1$ to the optical element 224. For example, rubber may fulfill the same function.

Figure 3B:
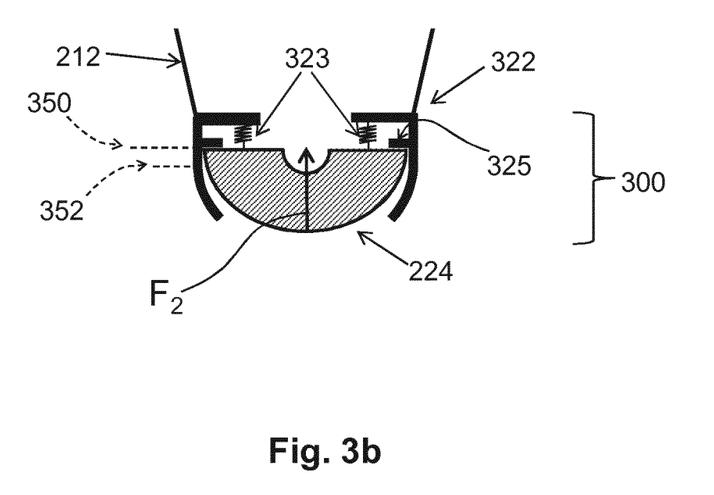

FIG. 3b schematically shows a cross-sectional view of an embodiment of the safety mechanism 300 wherein the optical element 224 is arranged at a treatment position 350. When the tip of the skin treatment device is pressed against the skin to be treated, the optical element 224 receives a second force $F_2$ in a second direction. The second direction is substantially perpendicular to the first direction. When the second force $F_2$ is larger than the first force $F_1$, the optical element 224 moves towards the movement limiting wall 325. The limiting wall 325 defines the treatment position. When the optical element 224 is in contact with the movement limiting wall 325, the spherical recess at the (back-) surface of the optical element 224 is proximate to the focal point of the light beam that impinges on the spherical recess and, thus, the optical element 224 does not much diverge the impinging light beam and a treatment light beam is obtained. The treatment position 352 is selected such that the obtained treatment light beam that exits the optical element 224 towards the skin is relatively narrow and is a substantially parallel light beam. In this context, "substantially parallel" means that the beam angle of the obtained treatment beam is smaller than 4° or, optionally, smaller than 2°. As soon as the optical element 224 is removed from contact with the skin, the optical element 224 does not receive the second force $F_2$ anymore and then the first force $F_1$ presses the optical element 224 back to the safety position 352.

The above discussed safety mechanism 300 is completely based on mechanical and optical elements. In general, such systems are fail-safe because they do not depend on electronic circuitry or specific actuators that must, for example, be activated by means of power. However, embodiments of safety mechanism 300 are not limited to the use of optical and mechanical elements only. Instead of the springs 323, one or more actuators may be used that are controlled by a circuitry in such a way that the actuators provide a force to the optical element 224 that moves the optical element 224 towards the safety position 352 when the tip of the skin treatment device is not in contact with the skin.

Figure 4A:
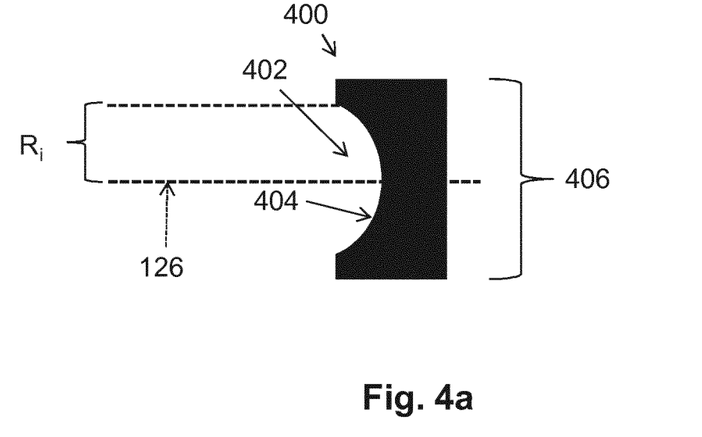
Figure 4B:
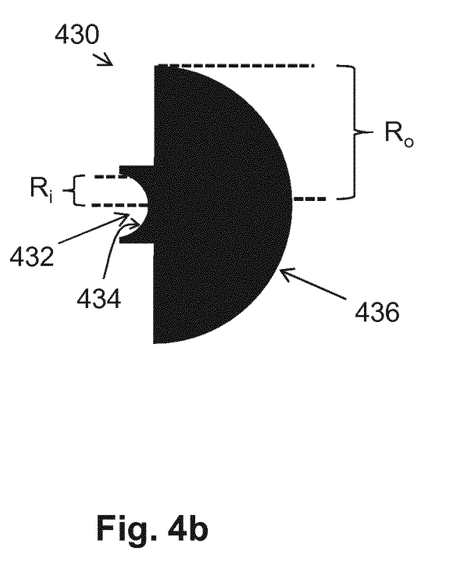
Figure 4C:
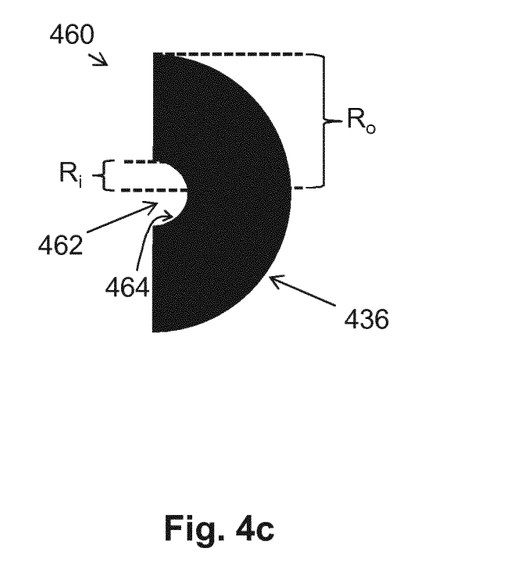

FIGS. 4a to 4c schematically show a cross-sectional view of embodiments of the optical element 400, 430, 460. All optical elements 400, 430 440 comprise a light entrance surface 404, 434, 464 for receiving an impinging light beam and comprise a light exit surface 406, 436 through which either the treatment light beam or the eye-safe light beam is transmitted.

Optical element 400 comprises a light entrance surface that is round and that is formed by a recess 402 in a light transmitting material. As a result, the light entrance surface 404 forms a diverging lens. The recess 402 has a radius $R_i$. The light exit surface 406 is a flat surface which has no lens function. When the light entrance surface 404 is arranged at a focal point of the impinging light beam, the diverging character of the light entrance surface 404 is cancelled and, thus, a position of the light entrance surface 404 proximate to the focal point is an advantageous position for obtaining a relatively narrow treatment light beam. When the light entrance surface 404 is arranged distant from the focal point of the impinging light beam, and when the radius of the impinging light beam at the position where it impinges on the light entrance surface 404 is only marginally smaller than the radius $R_t$ of the recess 402, the diverging character of the light entrance surface is used to a maximum extent and the impinging light beam is strongly diverged. Thus, in the safety position, the radius of the impinging light beam (as received from the light emission element) is about equal to the radius $R_t$ of the recess 402 and is at least not larger than the radius $R_t$ of the recess 402 because that would result in undesired scattering effects.

The light entrance surface 434 of the optical element 430 is also a round recess 432 in a light transmitting material that acts as a relatively strong diverging lens. The round recess 432 is made in a part that protrudes from the main body of the optical element. The light exit surface 436 is a smooth round surface which acts as a converging lens. The radius $R_i$ of the recess 432 is at least several times smaller than the radius $R_o$ of the round light exit surface 436, for example, at least 3 times smaller, or at least 5 times smaller. As a result, the converging character of the light exit surface 436 is smaller than the diverging character of the light entrance surface 434 and the optical element 430 as a whole acts as a diverging lens. The smooth, round light exit surface 436 has a shape that is comfortable for contacting the skin to be treated and for moving over the skin to be treated.

Optical element 460 is similar to optical element 430, however, the round recess 462 is not provided in an element that protrudes from the main body of the optical element, but is directly provided in the main body of the optical element and, therefore, optical element 460 may be cheaper because of manufacturing benefits.

A specific embodiment of a shape of the light entrance surface 404, 434, 464 is a shape that corresponds to a portion of a sphere, for example, a semi-sphere. A specific embodiment of a shape of the light exit surface 436 is a shape that corresponds to a portion of a sphere, for example, a semi-sphere.

Figure 5A:
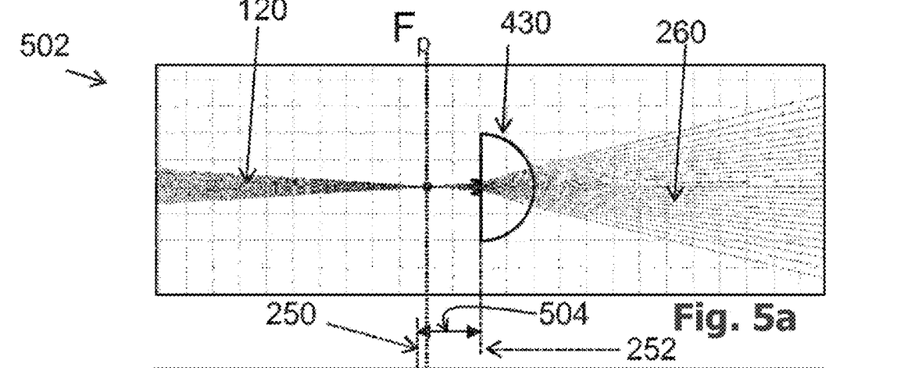
Figure 5B:
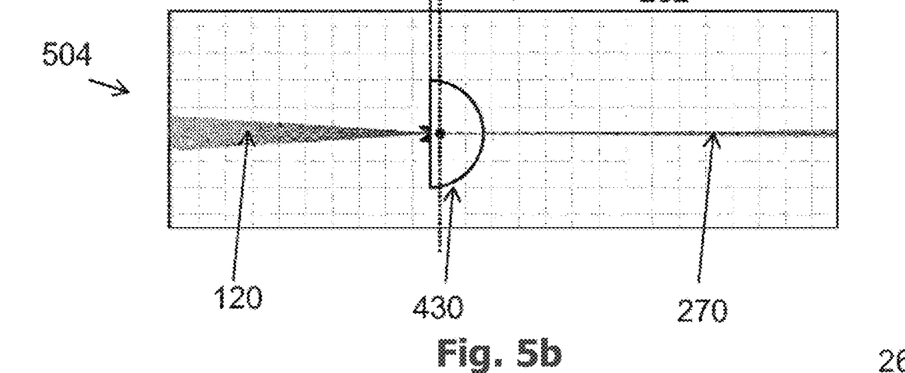

FIGS. 5a and 5b schematically shows results 502, 504, respectively, of a ray tracing simulation for situations in which the optical element 430 is arranged in the safety position 252 and in the treatment position 250, respectively. To the left of each simulation result 502, 504, a converging light beam 120 is drawn that is received from a light emission element of the skin treatment device (see e.g. FIG. 1). The converging light beam 120 is focused at focal point $F_p$. Beyond the focal point $F_p$ (assuming the optical element is not directly in front of or at the focal point $F_p$), which in FIGS. 5a and 5b is to the right of the focal point $F_p$, the light beam 120 diverges. In the simulation result 502 of FIG. 5a, it can be seen that the safety position 252 of the optical element 430 corresponds to a position of the light beam 120 where light beam 120 is already diverging. At the safety position 252, light beam 120 has a radius that is approximately equal to the radius of the round recess that forms the light entrance surface. At this position, the light entrance surface diverges the light beam to a relatively wide light beam. As seen in the simulation result 502, the converging effect of the light exit surface does not cancel out the diverging effect of the light entrance surface. As a result, the eye-safe light beam 260 is obtained.

Simulation result 504 of FIG. 5b shows the optical element 430 at its treatment position. The treatment position 250 is selected such that the cross-sectional shape of the obtained treatment light beam 270 is relatively small and such that the beam angle of the treatment light beam 270 is relatively small. For example, a diameter of the cross-sectional shape of the treatment light beam is less than 1 mm, wherein the cross-section of the treatment light beam 270 is measured at the light exit surface of optical element 430. For example, the beam angle of the treatment light beam 270 is smaller than 4° wherein the beam angle is measured within the optical element 430. Because the light beam 120 converges to the focal point $F_p$, the relatively narrow treatment light beam 270 can be obtained by positioning the light entrance surface of the optical element 430 close to the focal point $F_p$ and, optionally, slightly in front of the focal point $F_p$. In front of the focal point $F_p$ means, in this case, at a position where the light beam 120 is still converging to the focal point $F_p$, but where the diameter of the light beam 120 is relatively small.

The indicated distance 504 is the distance over which the optical element 430 moves along the optical axis from the treatment position 250 to the safety position 252, and vice versa.

Figure 5C:
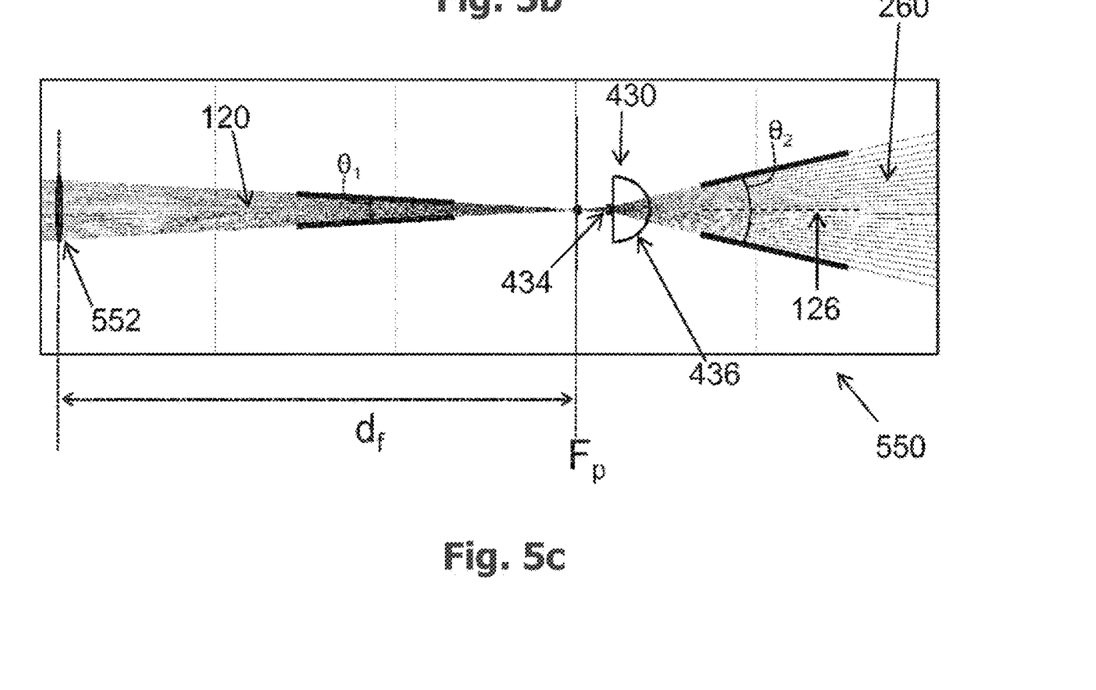

FIG. 5c schematically shows a result 550 of a ray tracing simulation, wherein also a lens 552 of the light emission element is taken into account. In the leftmost part of the figure, a substantially parallel light beam is received by the lens 552 of the light emission element. Such a substantially parallel light beam may be generated by, for example, a laser diode of the light emission element. The lens 552 has a focal distance $d_f$ and focuses the light beam 120 to its focal point $F_p$. The light beam 120 has a first beam angle $\Theta_1$. The optical element receives the light beam 120 at its light entrance surface 434 and emits a light beam at its light exit surface 436. The emitted light beam has a beam angle $\Theta_2$. In the example of FIG. 5c the optical element 430 is positioned at its safety position and, as such, the emitted light beam is the eye-safe light beam 260.

In an embodiment, the light entrance surface 434 and the light exit surface 436 have the shape of a semi-sphere. The light entrance surface 434 forms a lens that has a focal distance of −0.2 mm, and that has a 0.2 mm lens radius. The light exit surface 436 forms a lens that has a focal distance of 2 mm and that has a 2 mm lens radius. The lens 552 has, for example, a lens diameter of 2 mm and a focal distance of 30 mm and then the first beam angle $\theta_1$ is about 8°. The light entrance surface 434 is arranged at a position where the light beam is diverging and has a radius of about 2 mm. Then the second beam angle $\theta_2$ is about 30°. When the optical element 430 is in its treatment position, the second beam angle $\theta_2$ is smaller than 4° or, optionally, smaller than 2° or, optionally, smaller than 1°. Optionally, when the optical element 430 is in its treatment position, the light rays of the treatment light beam are arranged substantially in parallel.

Figure 6A:
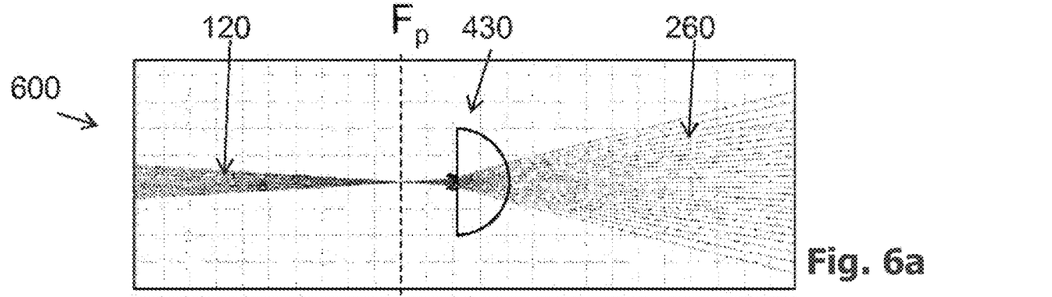
Figure 6B:
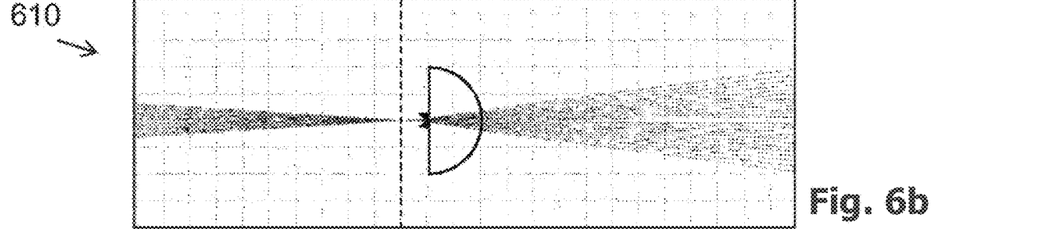
Figure 6C:
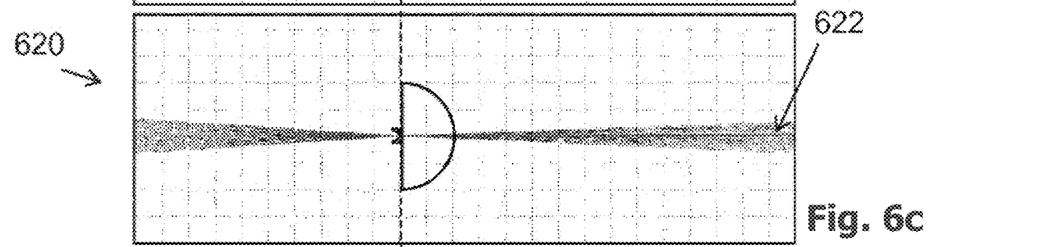
Figure 6D:
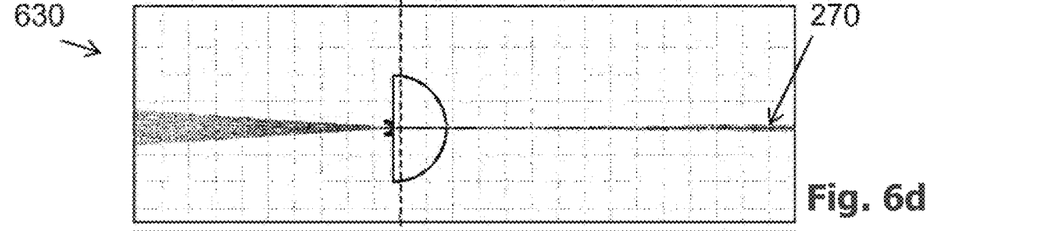
Figure 6E:
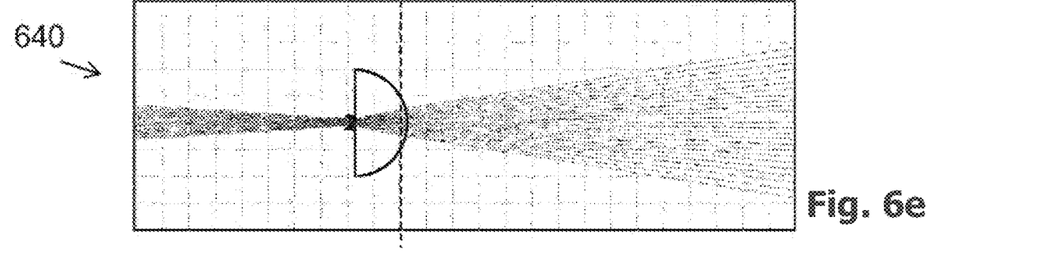

FIGS. 6a-6e schematically presents several results of ray-tracking simulations 600, 610, 620, 630, 640, respectively. Simulation result 600 of FIG. 6a shows how the received light beam 120 is refracted to the eye-safe light beam by the optical element 430 if the optical element 430 is in its safety position. Simulation result 630 of FIG. 6d shows a possible treatment position of the optical element in which a very narrow treatment light beam 270 is obtained at the light exit surface of the optical element. Simulation results 610 and 620 of FIGS. 6b and 6c, respectively, show intermediate positions of the optical element. In particular, simulation result 620 shows a position of the optical element such that the light entrance surface is exactly at the focal point Fp of the received light beam 120. At this position of the optical element, the diverging effect of the optical element is cancelled. Depending on the received light beam 120, at this position of the optical element a light beam 622 that is transmitted by the optical element is relatively narrow. When this light beam 622 is narrow enough to obtain a suitable treatment effect, e.g. when the light beam 622 has a beam angle of less than 4°, light beam 622 may also be the treatment light beam (and, thus, a position at the focal point may also be a treatment position). In the example of simulation results 640 of FIG. 6e, the optical element 430 is at a position where the received light beam 120 is still converging. At this position, the diverging effect of the optical element 430 changes the converging light beam into a diverging light beam, however, when this is compared to the eye-safe light beam 260, the beam angle is smaller than the beam angle of the eye-safe light beam 260.

In summary, the application provides a skin treatment device for locally treating skin with light. The skin treatment device comprises a tip, a light emission element, a safety mechanism comprising an optical element and an optical element positioning structure. The optical element receives a converging light beam from the light mission element. The optical element is configured to operate as a diverging lens. The optical element positioning structure positions the optical element in a safety position or in a treatment position when the tip is in contact with the skin to be treated and allows movement between both positions. In the safety position, the optical element is arranged at a position on the optical axis to generate an eye-safe light beam. In the treatment position, the optical element is arranged at another position on the optical axis to generate a treatment light beam.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A skin treatment device for locally treating skin with light, the skin treatment device comprising:
   a tip arranged and configured to be brought into contact with the skin;
   a light source arranged and configured to emit, in use, a light beam towards the tip along an optical axis, the light beam being a converging light beam, the optical axis extending in a longitudinal direction of the skin treatment device through the tip; and
   a diverging lens provided proximate to the tip in the light beam, wherein the diverging lens has on a first side, a light exit surface facing the tip and, on a second side opposite the first side, a light entrance surface facing the light source to receive the light beam; and
   wherein the diverging lens is movable via the tip along the optical axis between a treatment position when the tip is in contact with the skin and a safety position when the tip is not in contact with the skin,
   wherein, in the safety position, the light entrance surface of the diverging lens is arranged in the light beam at a first position on the optical axis to obtain an eye-safe light beam at the light exit surface, and
   wherein, in the treatment position, the light entrance surface of the diverging lens is arranged in the light beam at a second position on the optical axis at a distance proximal or distal from the first position to obtain a treatment light beam at the light exit surface.

2. The skin treatment device according to claim 1, further comprising a resilient element applying a first force to the diverging lens in a first direction parallel to the optical axis and away from the light source towards the safety position.

3. The skin treatment device according to claim 2, wherein the diverging element is arranged at the tip to receive a force (F2) in a second direction towards the treatment position when the tip is pressed to the skin for moving the diverging lens towards the treatment position, the second direction being opposite to the first direction.

4. The skin treatment device according to claim 3, further comprising:
   a housing including a front wall being arranged proximate to a skin contact surface of the tip for defining the safety position by limiting movement of the diverging lens in the first direction, the front wall including an opening for allowing the diverging lens to partially protrude from the housing if the diverging lens is arranged at the safety position; and
   a movement limiting wall arranged at a distance from the skin contact surface of the tip for defining the treatment position by limiting movement of the diverging lens in the second direction when the diverging lens is pressed to the skin.

5. The skin treatment device according to claim 1, wherein the light entrance surface is has a round shape.

6. The skin treatment device according to claim 1, wherein the light exit surface of the diverging lens has a round shape.

7. The skin treatment device according 1, wherein the light entrance surface of the diverging lens is a round shaped recess having a first radius (Ri), and wherein the light exit surface of the diverging lens has is a round shaped surface having a second radius (Ro), the second radius (Ro) being at least three times larger than the first radius (Ri).

8. The skin treatment device according to claim 1, wherein the diverging lens is made of a light transmitting material having a refractive index that matches a refractive index of human skin.

9. The skin treatment device according to claim 1, wherein the skin treatment device is configured to be operated by a hand of a user.

10. The skin treatment device according to claim 1, wherein the light source includes a laser for emitting the light beam and a lens for converging the light beam to a focal point (Fp) on the optical axis.

11. The skin treatment device according to claim 1, wherein the eye-safe light beam is a diverging light beam.

12. The skin treatment device according to claim 11, wherein a beam angle ($\Theta_2$) of the eye-safe light beam is larger than a beam angle ($\Theta_1$) of the light beam.

13. The skin treatment device according to claim 1, the treatment light beam is substantially parallel.

14. The skin treatment device according to claim 13, wherein the beam angle of the treatment light beam is smaller than 4°, and
   wherein a diameter of the treatment light beam, measured at the light exit surface, is smaller than 1 mm.

15. The skin treatment device according to claim 1, wherein the treatment position of the diverging lens along the optical axis is closer to a focal point of the light source along the optical axis than the safety position of the diverging lens along the optical axis.

16. The skin treatment device according to claim 1, wherein the light entrance surface of the diverging lens has a round shape.

17. The skin treatment device according to claim 7, the second radius (Ro) of the light exit surface is at least five times larger than the first radius (Ri) of the light entrance surface.

18. The skin treatment device according to claim 11, wherein a beam angle ($\Theta_2$) of the eye-safe light beam is larger than 20°.

19. The skin treatment device according to claim 1, wherein a radius of the light beam impinging on the light entrance surface when the diverging lens is in the safety position is greater than a radius of the light beam impinging on the light entrance surface when the diverging lens is in the treatment position.

20. The skin treatment device according to claim 1, wherein a radius of the light beam at the light exit surface when the diverging lens is in the safety position is greater than a radius of the light beam at the light exit surface when the diverging lens is in the treatment position.

* * * * *